(12) United States Patent
Song et al.

(10) Patent No.: US 11,414,650 B2
(45) Date of Patent: Aug. 16, 2022

(54) **CONSTRUCTION METHOD OF *MUCOR CIRCINELLOIDES* CELL FACTORY FOR PRODUCING DIHOMO-GAMMA-LINOLENIC ACID AND FERMENTATION TECHNOLOGY**

(71) Applicant: SHANDONG UNIVERSITY OF TECHNOLOGY, Zibo (CN)

(72) Inventors: Yuanda Song, Zibo (CN); Md. Ahsanul Kabir Khan, Zibo (CN); Junhuan Yang, Zibo (CN); Huaiyuan Zhang, Zibo (CN); Wu Yang, Zibo (CN); Qing Liu, Zibo (CN)

(73) Assignee: SHANDONG UNIVERSITY OF TECHNOLOGY, Shandong (CN)

( * ) Notice: Subject to any disclaimer, the term of this patent is extended or adjusted under 35 U.S.C. 154(b) by 0 days.

(21) Appl. No.: 17/120,163

(22) Filed: Dec. 12, 2020

(65) Prior Publication Data

US 2021/0102227 A1  Apr. 8, 2021

Related U.S. Application Data

(63) Continuation of application No. PCT/CN2019/124015, filed on Dec. 9, 2019.

(30) Foreign Application Priority Data

Dec. 11, 2018 (CN) .......................... 201811510570.X

(51) Int. Cl.
*C12N 9/02* (2006.01)
*C12P 7/64* (2022.01)
*C12P 7/6463* (2022.01)
*C12N 1/14* (2006.01)
*C12N 15/80* (2006.01)

(52) U.S. Cl.
CPC .......... *C12N 9/0071* (2013.01); *C12P 7/6463* (2013.01); *C12N 1/14* (2013.01); *C12N 15/80* (2013.01)

(58) Field of Classification Search
CPC ............................. C12N 9/0071; C12P 7/3463
See application file for complete search history.

(56) References Cited

U.S. PATENT DOCUMENTS

| 6,677,145 | B2* | 1/2004 | Mukerji | ..................... A61P 9/00 435/193 |
| 2003/0163845 | A1 | 8/2003 | Mukerji et al. | |
| 2017/0016015 | A1* | 1/2017 | Zank | ......................... C11B 1/00 |

FOREIGN PATENT DOCUMENTS

| CN | 110373437 A | 10/2019 |
| WO | 2000012720 A | 3/2000 |

OTHER PUBLICATIONS

Studer. Residue mutations and their impact on protein structure and function: detecting beneficial and pathogenic changes. Biochem. J. (2013) 449, 581-594.*
Zhang (Improved γ-linolenic acid production in Mucor circinelloides by homologous overexpressing of delta-12 and delta-6 desaturases. Microb Cell Fact. Jun. 21, 2017;16(1):113.*
Xiao Ruan, Improved Gama-linolenic acid production in Mucor circinelloides by homologous overexpressing of desaturases, Master's Thesis, Jiangnan University, Jun. 2015.
Shi et al., Molecular mechanism of subsliale specifi city for delta 6 desaturase from Mortierella alpina and Micromonas pusilia, Journal of Lipid Research, vol. 56, pp. 2309-2321 (Oct. 20, 2015).
Ge et al., Application of a omega-3 Desaturase with an Arachidonic Acid Preference to Eicosapentaenoic Acid Production in Mortierella alpina, Front. Bioeng. Biotechnol. vol. 5, Article 89, pp. 1-10 (Jan. 22, 2018).
Khan et al., Construction of!DGLA producing cell factory by genetic modification of Mucor circinelloides, Microbial Cell Factories, No. 64, Article 68 (Apr. 3, 2019).

* cited by examiner

Primary Examiner — Yong D Pak
(74) Attorney, Agent, or Firm — SZDC Law P.C.

(57) ABSTRACT

The present disclosure relates to a construction method of a *Mucor circinelloides* cell factory for producing dihomo-γ-linolenic acid and a fermentation technology, belonging to the field of genetic engineering. In the present disclosure, γ-linolenic acid elongase gene glelo is obtained from *Mortierella alpine* by cloning, the gene is ligated to an integrative plasmid pMAT1552, and transformed into a *Mucor circinelloides* defective strain Mu402, and the gene glelo is integrated into Mucor circinelloides genome through homologous recombination, to obtain the recombinant strain Mc-glelo, and finally, the expression of the gene glelo in *Mucor circinelloides* is realized. The lipid content in the recombinant strain Mc-glelo is not obviously different from that in the control strain Mc1552, however, the lipid composition changes greatly, and dihomo-γ-linolenic acid appears in the lipids of the recombinant strain Mc-glelo, and the content thereof reaches 5.7% of the total fatty acids. Under optimized fermentation conditions and in the presence of precursor fatty acid, the DGLA content reaches 7.6%. The new recombinant strain was deposited in China General Microbiological Culture Collection Center on Jun. 20, 2018, with the address of No. 3, Courtyard 1, Beichen West Road, Chaoyang District, Beijing. The accession number given to the biological material by the collection center is CGMCC No. 15887, and the suggested taxonomic denomination is *Mucor circinelloides*-GLELO.

9 Claims, 1 Drawing Sheet
Specification includes a Sequence Listing.

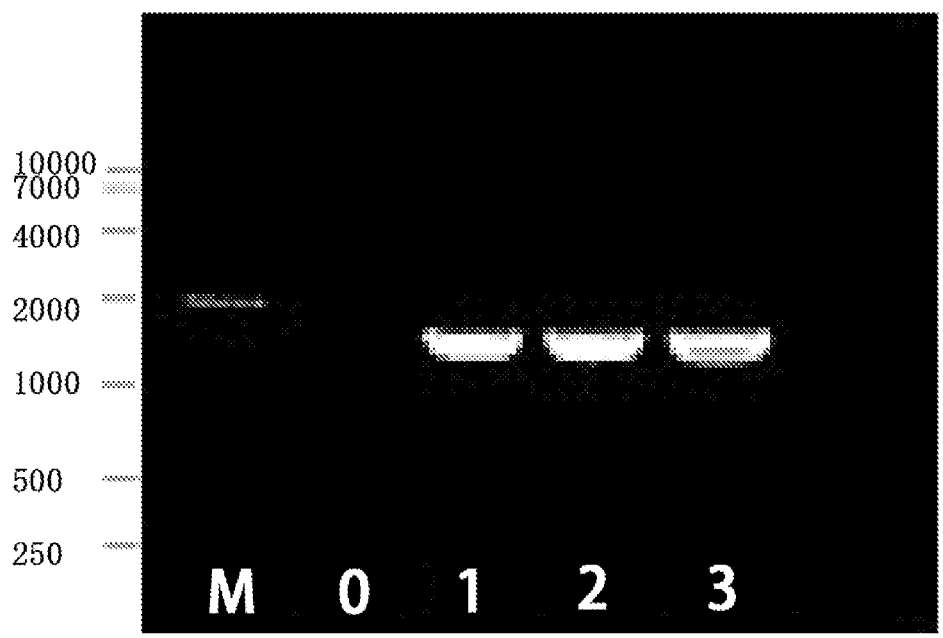

SEQUENCE LISTING

<160> NUMBER OF SEQ ID NOS: 5

<210> SEQ ID NO 1
<211> LENGTH: 957
<212> TYPE: DNA
<213> ORGANISM: Mortierella alpina

<400> SEQUENCE: 1

```
atggagtcga ttgcgccatt cctcccatca aagatgccgc aagatctgtt tatggacctt      60
gccaccgcta tcggtgtccg ggccgcgccc tatgtcgatc ctctcgaggc cgcgctggtg     120
gcccaggccg agaagtacat ccccacgatt gtccatcaca cgcgtgggtt cctggtcgcg     180
gtggagtcgc ctttggcccg tgagctgccg ttgatgaacc cgttccacgt gctgttgatc     240
gtgctcgctt atttggtcac ggtctttgtg ggcatgcaga tcatgaagaa ctttgagcgg     300
ttcgaggtca agacgttttc gctcctgcac aacttttgtc tggtctcgat cagcgcctac     360
atgtgcggtg ggatcctgta cgaggcttat caggccaact atggactgtt tgagaacgct     420
gctgatcata ccttcaaggg tcttcctatg gccaagatga tctggctctt ctacttctcc     480
aagatcatgg agtttgtcga caccatgatc atggtcctca gaagaacaa ccgccagatc     540
tccttcttgc acgtttacca ccacagctcc atcttcacca tctggtggtt ggtcaccttt     600
gttgcaccca acggtgaagc ctacttctct gctgcgttga actcgttcat ccatgtgatc     660
atgtacggct actacttctt gtcggccttg gcttcaagc aggtgtcgtt catcaagttc     720
tacatcacgc gctcgcagat gacacagttc tgcatgatgt cggtccagtc ttcctgggac     780
atgtacgcca tgaaggtcct tggccgcccc ggatacccct tcttcatcac ggctctgctt     840
tggttctaca tgtggaccat gctcggtctc ttctacaact tttacagaaa gaacgccaag     900
ttggccaagc aggccaaggc cgacgctgcc aaggagaagg caaggaagtt gcagtaa       957
```

<210> SEQ ID NO 2
<211> LENGTH: 51
<212> TYPE: DNA
<213> ORGANISM: Artificial Sequence
<220> FEATURE:
<223> OTHER INFORMATION: Primer

<400> SEQUENCE: 2

```
acttttatat acaaaataac taaatctcga gatggagtcg attgcgccat t              51
```

<210> SEQ ID NO 3
<211> LENGTH: 46
<212> TYPE: DNA
<213> ORGANISM: Artificial Sequence
<220> FEATURE:
<223> OTHER INFORMATION: Primer

<400> SEQUENCE: 3

```
actagtcgca attgccgcgg ctcgagttac tgcaacttcc ttgcct                    46
```

<210> SEQ ID NO 4
<211> LENGTH: 29
<212> TYPE: DNA
<213> ORGANISM: Artificial Sequence
<220> FEATURE:
<223> OTHER INFORMATION: Primer

<400> SEQUENCE: 4

```
cctcggcgtc atgatgtttt tgtgtacct                                       29
```

```
<210> SEQ ID NO 5
<211> LENGTH: 27
<212> TYPE: DNA
<213> ORGANISM: Artificial Sequence
<220> FEATURE:
<223> OTHER INFORMATION: Primer

<400> SEQUENCE: 5
gggatgtctg ctgctaccat gtctcat                                              27
```

CONSTRUCTION METHOD OF *MUCOR CIRCINELLOIDES* CELL FACTORY FOR PRODUCING DIHOMO-GAMMA-LINOLENIC ACID AND FERMENTATION TECHNOLOGY

CROSS-REFERENCE TO RELATED APPLICATIONS

The present is a Continuation Application of PCT/CN2019/124015, filed on Dec. 9, 2019, which claims the priority of the Chinese patent application No. 201811510570.X, filed with the Chinese Patent Office on Dec. 11, 2018 and entitled "Construction Method of *Mucor circinelloides* Cell Factory for Producing Dihomo-γ-linolenic Acid and Fermentation Technology", which is incorporated herein by reference in its entirety.

TECHNICAL FIELD

The present disclosure relates to a construction method of a *Mucor circinelloides* cell factory for producing dihomo-γ-linolenic acid and a fermentation technology, belonging to the field of genetic engineering. In the present disclosure, by the technology of homologous recombination, a γ-linolenic acid elongase gene (glelo) derived from *Mortierella alpina* is expressed in *Mucor circinelloides*, and thus a cell factory capable of producing dihomo-γ-linolenic acid is constructed.

BACKGROUND ART

Polyunsaturated fatty acids (PUFAs) are gaining increasing attention due to their numerous nutritional and health benefits to the human body. In mammals, including humans, only saturated fatty acids (SAFA) and monounsaturated fatty acids (MUFA) can be synthesized in vivo, while ω-6 and ω-3 polyunsaturated fatty acids, such as linoleic acids (LA, 18:2, n-6) and α-linolenic acid (ALA, 18:3, n-3), cannot be synthesized in vivo. Hence, polyunsaturated fatty acids are essential fatty acids for the human body, and can only be gotten from diet. After being catalyzed by various enzymes, linoleic acid and linolenic acid can be used for synthesizing docosapentaenoic acid (DPA, 22:5, n-6) and docosahexaenoic acid (DHA, 22:5, n-3). Upon researches, it has been found that occurrence of various diseases, such as obesity, hypertension, diabetes, coronary atherosclerosis, schizophrenia and senile dementia, is associated with the metabolism of essential fatty acids. Therefore, essential fatty acids and their derivatives are of significance in both physiology and pathology for human health.

Dihomo-γ-linolenic acid (DGLA, 20:3, n-6) is synthesized by reaction of γ-linolenic acid (GLA, 18:3, n-6) in the presence of Δ6 elongase. Dihomo-γ-linolenic acid has important physiological functions, from which, in oxidative metabolism, under the catalysis of cyclooxygenase and fat synthase, anti-inflammatory eicosanoids such as prostaglandin E1 and leukotriene E3 can be produced. Moreover, dihomo-γ-linolenic acid is converted into arachidonic acid (AA, 20:4, n-6) in the presence of Δ5 desaturase, and arachidonic acid is a precursor of prostaglandin E2 and leukotriene B3.

Microorganisms, in which 20% or more of lipids are able to be intracellularly accumulated, are called oleaginous microorganisms, including bacteria, fungi, *Saccharomycetes* and microalgae. Among lipid-producing fungi, *Mucor circinelloides* were used for industrial production of GLA in the 1980s. *Mucor circinelloides* have been used as model organisms for studying the production of GLA by microorganisms, due to its high the lipid-producing ability, the genomes thereof have been sequenced, and the genetic research system has been well established.

*Mortierella alpina* is another lipid-producing microorganism whose lipid yield can reach 50% of the dry weight of cells and whose arachidonic acid content is relatively high. Therefore, *Mortierella alpina* is used for the industrial production of arachidonic acid. In recent years, many studies have been made on genes related to lipid production in *Mortierella alpina*, and the lipid synthesis pathway thereof has been studied in detail. Δ6 elongase is capable of catalyzing the elongation of GLA (18:3, n-6) to dihomo-γ-linolenic acid (20:3, n-6). Thus, the gene coding Δ6 elongase is named γ-linolenic acid elongase gene (glelo). This gene is a rate-limiting factor for arachidonic acid biosynthesis in *Mortierella alpina*. However, there are few studies on the production of dihomo-γ-linolenic acid (DGLA, 20:3, n-6) using glelo-expressing microorganisms.

*Mortierella alpina* has both relatively high oil yield and polyunsaturated fatty acid content, but its fermentation cost is relatively high and biomass is low, which limits the industrial application thereof. Previous studies in our laboratory found that the content of γ-linolenic acid was 18-19% in total fatty acids of the *Mucor circinelloides* cell, there was substantially no DGLA in the cell, but the fermentation conditions thereof were highly controllable and the biomass was high. Therefore, this study combines the advantages of two strains, and allows the glelo gene derived from *Mortierella alpina* to be expressed in *Mucor circinelloides* by the genetic engineering method of homologous recombination, to construct a cell factory capable of producing DGLA, so as to provide guidance for promoting the industrial production of DGLA by *Mucor circinelloides*.

SUMMARY

The present disclosure provides a construction and fermentation method of a *Mucor circinelloides* cell factory for producing dihomo-γ-linolenic acid, comprising introducing γ-linolenic acid elongase gene glelo obtained by cloning from a *Mortierella alpina* strain into *Mucor circinelloides* by the method of homologous recombination to obtain a *Mucor circinelloides* recombinant strain Mc-glelo, and fermenting the same by an optimized fermentation process to obtain functional lipid DGLA with a content of up to 7.6%.

In one or more embodiments, a method for preparing the recombinant strain Mc-glelo comprises performing PCR with designed primers using total cDNA of *Mortierella alpine* as a template to obtain gene glelo encoding γ-linolenic acid elongase, whose nucleotide sequence is shown in SEQ ID NO: 1, ligating the gene to an integrative plasmid pMAT1552, and then performing electricotransformation of the recombinant plasmid into a protoplast of a *Mucor circinelloides* deficient strain Mu402, and selecting positive clones for fermentation culture.

In one or more embodiments, the optimized fermentation process comprises adding 1-3% safflower seed oil or sunflower seed oil to the Kendrik medium and culturing recombinant *Mucor circinelloides* cells under optimal fermentation parameters.

The present disclosure provides a recombinant cell producing dihomo-γ-linolenic acid, wherein, the recombinant cell comprises a polynucleotide encoding γ-linolenic acid elongase, the polynucleotide encoding γ-linolenic acid elongase being operably linked to a promoter capable of driving expression of the polynucleotide in the cell.

In one or more embodiments, the recombinant cell is not derived from *Mortierella alpina*.

In one or more embodiments, the polynucleotide encoding γ-linolenic acid elongase comprises:
(1) a polynucleotide sequence shown in SEQ ID NO: 1;
(2) a polynucleotide sequence with at least 50%, preferably at least 60%, more preferably at least 70%, more preferably at least 80%, more preferably at least 90%, more preferably at least 95% identity to the polynucleotide sequence shown in SEQ ID NO: 1; or
(3) a polynucleotide sequence encoding a biologically active fragment in the polynucleotide sequence of (1) or (2).

In one or more embodiments, the recombinant cell is derived from a microbial cell, a plant cell, or a microalgae cell.

In one or more embodiments, the recombinant cell is derived from a microbial cell.

In one or more embodiments, the microbial cell of wild type substantially produces no dihomo-γ-linolenic acid.

In one or more embodiments, the microbial cell of wild type produces γ-linolenic acid, γ-linolenic acid compounds, and/or precursor compounds of γ-linolenic acid.

In one or more embodiments, the content of γ-linolenic acid in total fatty acids of the microbial cell of wild type is greater than 10%, for example, greater than 12%, for example, greater than 14%, for example, greater than 16%, and for example, greater than 18%.

In one or more embodiments, the recombinant cell is derived from a fungal cell.

In one or more embodiments, the recombinant cell is derived from a *Mucor* cell.

In one or more embodiments, the recombinant cell is derived from a *Mucor circinelloides* cell.

The present disclosure provides a method for preparing a recombinant cell producing dihomo-γ-linolenic acid in the present disclosure, the method comprising introducing into a cell a polynucleotide encoding γ-linolenic acid elongase, wherein the polynucleotide encoding γ-linolenic acid elongase is operably linked to a promoter capable of driving expression of the polynucleotide in the cell.

The present disclosure provides a method for producing dihomo-γ-linolenic acid, comprising fermenting the recombinant cell producing dihomo-γ-linolenic acid in the present disclosure.

In one or more embodiments, the fermentation is performed in a fermentation medium comprising γ-linolenic acid, γ-linolenic acid compounds or precursor compounds of γ-linolenic acid.

In one or more embodiments, the fermentation medium contains linoleic acid and/or linoleic acid compounds.

In one or more embodiments, the fermentation medium contains vegetable oil containing linoleic acid and/or linoleic acid compounds.

In one or more embodiments, the vegetable oil is safflower seed oil or sunflower seed oil.

In one or more embodiments, the vegetable oil is initially present in the fermentation medium, or is added to the fermentation medium by feeding during the fermentation.

The present disclosure provides a *Mucor circinelloides* recombinant strain Mc-glelo, comprising γ-linolenic acid elongase gene (glelo) integrated on *Mucor circinelloides* genome and capable of integrative expression. Compared with the control strain Mc1552, the fatty acid composition is changed and the content of dihomo-γ-linolenic acid (DGLA) reaches 5.7%. The content of DGLA reaches 7.6% by adding precursor fatty acids and optimizing the fermentation conditions.

The technical solution of the present disclosure is: extracting mRNA of *Mortierella alpina* strain, obtaining cDNA by reverse transcription, designing specific primers, performing PCR amplification of glelo (the nucleotide sequence of which is shown in SEQ ID NO: 1), ligating the gene to the integrative plasmid pMAT1552, then performing electricotransformation of the recombinant plasmid to a protoplast of *Mucor circinelloides* deficient strain Mu402, and selecting positive clones for fermentation culture under the following fermentation conditions: using Kendrick or modified Kendrick medium, 28° C., 700 rpm, an air inflow of 1 v/v $min^{-1}$, and pH 6.0. In the fermentation process, samples are collected according to the lipid accumulation rule, for determination of lipid content and composition.

The present disclosure further provides a gene glelo encoding γ-linolenic acid elongase, the gene nucleic acid sequence of which is shown in SEQ ID NO: 1.

The present disclosure further provides an expression vector containing SEQ ID NO: 1, capable of expressing the glelo gene, the vector being an expression vector for *Mucor circinelloides*.

The new recombinant strain was deposited on Jun. 20, 2018 in China General Microbiological Culture Collection Center, with the address of No. 3, Courtyard 1, Beichen West Road, Chaoyang District, Beijing. The accession number given to the biological material by the collection center is CGMCC No. 15887, and the suggested taxonomic denomination is *Mucor circinelloides*-GLELO.

ADVANTAGEOUS EFFECTS

The advantageous effects of the present disclosure include, for example: the present disclosure provides a construction method of a *Mucor circinelloides* cell factory for producing dihomo-γ-linolenic acid and a fermentation technology; the content of DGLA in the recombinant strain Mc-glelo can reach 5.7% of the total fatty acids; and the content of DGLA reaches 7.6% by adding precursor fatty acids and optimizing the fermentation conditions.

BRIEF DESCRIPTION OF DRAWINGS

In order to more clearly illustrate technical solutions of embodiments of the present disclosure, the accompanying drawing which need to be used in the embodiments will be introduced below briefly.

FIG. 1 is a PCR verification result chart of a *Mucor circinelloides* recombinant strain, wherein M represents a standard protein molecular weight; 0 represents a control strain Mc1552; and 1-3 represent *Mucor circinelloides* recombinant strains Mc-glelo.

DETAILED DESCRIPTION OF EMBODIMENTS

In order to make objects, technical solutions and advantages of the embodiments of the present disclosure clearer, the technical solutions in the embodiments of the present disclosure will be described clearly and completely below. If no specific conditions are specified in the embodiments, they are carried out under normal conditions or conditions recommended by the manufacturer. If the manufacturers of reagents or apparatus used are not specified, they are conventional products commercially available.

Unless otherwise defined herein, scientific and technical terms used in connection with the present disclosure should have meanings that are commonly understood by those ordinarily skilled in the art. Exemplary methods and materials are described below, but methods and materials similar or equivalent to those described herein can also be used in the practice or test of the present disclosure.

As used herein, "identity", "identity percentage" or "identity %" refers to a relationship of two or more nucleotide sequences (or polypeptide sequences) to one another as determined by sequence comparison. Identity may represent the degree of correlation of sequences between polynucleotides (or polypeptide sequences), and may be determined by the match between strings of such sequences. In one or more embodiments, the identity percentage of two sequences, whether nucleotide or amino acid sequences, is obtained by dividing the number of exact matches between the two compared sequences by the length of a shorter sequence, and then multiplying the result by 100%. For example, the polynucleotide encoding γ-linolenic acid elongase includes a polynucleotide sequence having at least 50%, or at least 60%, or at least 70%, or at least 80%, or at least 85%, or at least 90%, or at least 95%, or at least 98%, or at least 99% identity to the polynucleotide sequence represented by SEQ ID No: 1.

In one or more embodiments, the recombinant cell may be a cell of an organism suitable for fermentation, for example, a unicellular microorganism, which may be a prokaryote or a eukaryote such as yeast, or a plant cell. In one or more embodiments, the cell is a microbial cell. In one or more embodiments, the cell is a fungal cell.

In one or more embodiments, the recombinant cell of the present disclosure can be obtained upon transformation of a nucleic acid molecule into a cell accomplished by any method that involves introducing the nucleic acid molecule into the cell. Transformation techniques include, but are not limited to, transfection, electroporation, microinjection, lipofection, adsorption, and protoplast fusion. The recombinant cell may remain unicellular or may grow into tissue, organ or multicellular organism. The transformed nucleic acid molecule may remain extrachromosomal or the transformed nucleic acid molecule may be integrated into one or more sites within the chromosome of the transformed cell (i.e., recombinant cell) in a manner that it retains its ability to be expressed.

In one or more embodiments, transformation of a nucleic acid molecule into a cell may be mediated by a recombinant vector. One type of recombinant vector includes a nucleic acid molecule of the present disclosure operably ligated to an expression vector. As indicated above, the words "operably ligate" refers to inserting a nucleic acid molecule into an expression vector in such a manner that the nucleic acid molecule can be expressed. The expression vector (which may be a DNA or RNA vector) is then capable of transforming a host cell and effecting expression of a specific nucleic acid molecule. In one or more embodiments, the expression vector is also capable of replication in a host cell. The expression vector may be a prokaryotic vector or a eukaryotic vector, and is typically virus or plasmid. The expression vector in the present disclosure includes any vector that is capable of functioning (i.e., directing gene expression) within a recombinant cell of the present disclosure.

As used herein, the term "biologically active fragment" herein refers to a portion of a given polypeptide/enzyme that still retains desaturase activity. These biologically active fragments can be readily determined by making a series of deletions to the full-length protein and testing activity of the resulting fragments.

When compared with a naturally occurring molecule, polynucleotides of the present disclosure may have one or more mutations that are deletions, insertions, or substitutions of nucleotide residues. The mutant may be naturally occurring (that is to say, isolated from a natural source) or synthesized (for example, synthesized by site-directed mutagenesis of a nucleic acid).

EXAMPLE 1: Cloning of *Mortierella alpina* γ-Linolenic Acid Elongase Gene Glelo

A *Mortierella alpina* strain was inoculated into a 500 mL Erlenmeyer flask equipped with a baffle and containing 100 mL of Kendrick medium (30 g/L glucose, 1.5 g/L $MgSO_4 \cdot 7H_2O$, 3.3 g/L ammonium tartrate, 7.0 g/L $KH_2PO_4$, 2.0 g/L $Na_2HPO_4$, 1.5 g/L yeast extract, 0.076 g/L $CaCl_2$, 8 mg/L $FeCl_3 \cdot 6H_2O$, 1 mg/L $ZnSO_4 \cdot 7H_2O$, 0.1 mg/L $CuSO_4 \cdot 5H_2O$, 0.1 mg/L $Co(NO_3)_2 \cdot 6H_2O$, 0.1 mg/L $MnSO_4 \cdot 5H_2O$), cultured for 48 h at the temperature of 28° C. and at a rotational speed of 150 rpm, and cells were collected by suction filtration. RNA was extracted, and reversely transcribed into cDNA, which was carried out with reference to instructions of a reverse transcription kit. According to the genome information of *Mortierella alpina* in NCBI (https://www.ncbi.nlm.nih.gov/) database, γ-linolenic acid elongase gene glelo (AF206662.1, 957 bp) was found, whose nucleotide sequence was as shown in SEQ ID NO: 1 below.

```
                                          SEQ ID NO: 1
atggagtcga  ttgcgccatt  cctcccatca  aagatgccgc
aagatctgtt  tatggacctt gccaccgcta  tcggtgtccg  ggccgcgccc  tatgtcgatc
ctctcgaggc  cgcgctggtg gcccaggccg  agaagtacat  ccccacgatt  gtccatcaca
cgcgtgggtt  cctggtcgcg gtggagtcgc  ctttggcccg  tgagctgccg  ttgatgaacc
cgttccacgt  gctgttgatc gtgctcgctt  atttggtcac  ggtctttgtg  ggcatgcaga
tcatgaagaa  ctttgagcgg ttcgaggtca  agacgttttc  gctcctgcac  aacttttgtc
tggtctcgat  cagcgcctac atgtgcggtg  ggatcctgta  cgaggcttat  caggccaact
atggactgtt  tgagaacgct gctgatcata  ccttcaaggg  tcttcctatg  gccaagatga
tctggctctt  ctacttctcc aagatcatgg  agtttgtcga  caccatgatc  atggtcctca
agaagaacaa  ccgccagatc tccttcttgc  acgtttacca  ccacagctcc  atcttcacca
tctggtggtt  ggtcaccttt gttgcaccca  acggtgaagc  ctacttctct  gctgcgttga
actcgttcat  ccatgtgatc atgtacggct  actacttctt  gtcggccttg  ggcttcaagc
aggtgtcgtt  catcaagttc tacatcacgc  gctcgcagat  gacacagttc  tgcatgatgt
cggtccagtc  ttcctgggac
```

-continued

```
atgtacgcca tgaaggtcct tggccgcccc ggatacccct
tcttcatcac ggctctgctt tggttctaca tgtggaccat gctcggtctc ttctacaact
tttacagaaa gaacgccaag ttggccaagc aggccaaggc cgacgctgcc aaggagaagg
caaggaagtt gcagtaa.
```

Specific primers GLELO-F and GLELO-R were designed according to the gene sequence, and PCR was carried out taking *Mortierella alpina* cDNA as a template.

```
GLELO-F:
                                       (SEQ ID NO: 2)
5'-ACTTTTATATACAAAATAACTAAATCTCGAGATGGAGTCGATTGC

GCCATT-3'

GLELO-R:
                                       (SEQ ID NO: 3)
5'-ACTAGTCGCAATTGCCGCGGCTCGAGTTACTGCAACTTCCTTGCC

T-3'
```

A 50 µL PCR reaction system: 10 µL of 5×PS buffer solution, 5 µL of dNTP mixture (each 2 mM), 1 µL of upstream primer, 1 µL of downstream primer, 100~200 ng of total cDNA, 1 µL of PrimeSTAR HS DNA polymerase, and ddH$_2$O for complementation to 50 µL. Reaction procedure is as follows: denaturing at 95° C. for 3 min, performing 30 cycles of denaturing at 95° C. for 30 sec, annealing at 54° C. for 30 sec and extending at 72° C. for 1.5 min, then extending again at 72° C. for 10 min, and reducing the temperature to 4° C. and keeping the temperature for 5 min. A 957 bp PCR fragment was obtained from amplification, the recovered fragment was ligated with a pMAT1552 vector, a ligation product was transformed to *Escherichia coli* Top10 competent cell, a transformation product was spread on a LB plate (10 g/L peptone, 5 g/L yeast extract, 10 g/L NaCl, and 1.5% agar) containing 100 mg/L ampicillin. The cells on the LB plate were cultured at 37° C. overnight, colonies were selected, and inoculated into an LB liquid culture medium (10 g/L peptone, 5 g/L yeast extract, and 10 g/L NaCl), after cultured for 8~10 h, plasmids were extracted for sequencing, and the plasmids with correct sequences were named as pMAT1552-glelo.

Preparation of *Mucor circinelloides* protoplasts: spores of *Mucor circinelloides* Mu402 strain were inoculated onto plate of YPG medium (3 g/L yeast extract, 10 g/L peptone, 20 g/L glucose, 20 µg/mL leucine, 200 µg/mL uracil, pH 4.5) and cultured at 28° C. for 1 day. The monoclonal mycelia were taken and dot-planted on a plate of YPG medium, and cultured at 28° C. for 3~4 days, to provide well-growing spores. To each plate, on which the spores grew well, 5~6 mL of YPG medium was added, the spores were taken by scraping with a sterilized spreading rod, a spore suspension was collected in a sterilized 50 mL centrifuge tube, and the concentration was calculated with a hemocytometer and the spore concentration was adjusted to 1×10$^7$/mL with YPG with pH 4.5. 12.5 mL of the above spore suspension was placed in a sterilized 250 mL Erlenmeyer flask, and placed in a refrigerator at 4° C. overnight to allow the spores to fully absorb water and swell. The Erlenmeyer flask was then placed on a shaker for culturing the spores at 30° C. and 250 rpm until the spores germinated. After centrifugation at 1100 rpm, the spores were washed twice with 5 mL of PS buffer with pH 6.5 [18.22 g of sorbitol and 20 mL of PBS buffer (137 mM NaCl, 2.7 mM KCl, 10 mM Na$_2$HPO$_4$, 2 mM KH$_2$PO$_4$)], to wash away the culture medium. The cultures were resuspended in 5 mL of PS buffer, and lyase at a final concentration of 4 mg/mL and 0.06 U/mL chitosanase were added, followed by incubation on a shaker at 30° C. and 60 rpm for 90 min so as to remove cell walls. After centrifugation at 100× g, the precipitates were washed twice with 0.5 M sorbitol pre-cooled at 4° C., and 800 µL of 0.5 M sorbitol was added, followed by gentle pipetting for resuspension of the precipitates to obtain protoplasts, which were dispensed in tubes for later use, 100 µL in each tube.

Construction of recombinant strain Mc-glelo: 100 µL of the protoplasts prepared above were well mixed with 1 µg of plasmids pMAT1552-glelo or pMAT1552 to be subjected, performing electrotransformation, after the electrotransformation, 1 mL of pre-cooled YPGS (0.5 mol/L sorbitol, 3 g/L yeast extract, 10 g/L peptone, and 20 g/L glucose) was immediately added, for incubation at 26° C. and 100 rpm for 1 h, followed by centrifugation at 100× g to remove YPGS, after being resuspended in YNBS [91.1 g/L sorbitol, 1.5 g/L glutamic acid, 1.5 g/L (NH$_4$)$_2$SO$_4$, 0.5 g/L yeast basic nitrogen source, 10 g/L glucose, pH adjustment to 4.5, and after sterilization, thiamine and nicotinic acid were added to a final concentration of 1 µg/mL], the suspension was uniformly spread on an MMC selective medium [10 g/L casein amino acid, 0.5 g/L yeast basic nitrogen source, 20 g/L glucose, and 15 g/L agar, pH adjustment to 3.2, and after sterilization, thiamine and nicotinic acid were added to a final concentration of 1 µg/mL], followed by culturing in darkness at 28° C. for 3~4 days. Single colony mycelia growing on 8 selective plates were randomly selected and inoculated on a new MMC plate, and cultured at 28° C. for 2-3 days to collect spores. About 200-300 spores were respectively inoculated to the MMC plate and the MMC plate containing uracil, and cultured at 28° C. for 2-3 days, followed by counting. The above screening steps were repeated until the number of the spores growing on the two plates was substantially the same, which indicated that the genetically stable transformants were obtained. The mycelia of the genetically stable transformant were cultured on a YPG medium plate at 30° C. for 5-7 days, then spores were collected, the concentration of the spores was adjusted to 1×10$^7$/mL, and the spores were stored in a 30% glycerin tube at −80° C. Finally, the *Mucor circinelloides* recombinant strain Mc-glelo and the control strain Mc1552 were obtained. The cells were cultured in shake flask after spreading and separated by vacuum filtration with a Buchner funnel, and the *Mucor circinelloides* genomic DNA was extracted (which was carried out by referring to the instructions of a plant rapid DNA extraction kit), which was taken as a template for PCR verification with 1552-F and 1552-R as primers (this pair of primers were corresponding to positions 300 bp upstream and downstream away from insertion site of target gene in the plasmid).

```
1552-F:
                                       (SEQ ID NO: 4)
5'-CCTCGGCGTCATGATGTTTTTGTGTACCT-3'

1552-R:
                                       (SEQ ID NO: 5)
5'-GGGATGTCTGCTGCTACCATGTCTCAT-3'
```

The reaction system and amplification conditions were as follows: pre-denaturation at 95° C. for 3 min, denaturation at 95° C. for 30 sec, annealing at 60° C. for 30 sec, extension at 72° C. for 2 min, 30 cycles, and extension again at 72° C. for 10 min. The PCR verification results are shown as in FIG. 1. A fragment obtained from the *Mucor circinelloides* recombinant strain Mc-glelo was 1557 bp, while a fragment obtained at the corresponding position of the control strain Mc1552 was 600 bp, which indicated that the plasmids had been successfully transformed into the *Mucor circinelloides*.

(1) Determination of fatty acid composition and content of *Mucor circinelloides* recombinant strain Mc-glelo Preparation of sample to be tested: the *Mucor circinelloides* recombinant strain Mc-glelo was cultured in a 2 L fermentation tank using Kendrick medium. The fermentation conditions were as follows: 28° C., 700 rpm, an air inflow of 1 v/v min$^{-1}$, and pH being maintained at 6.0. According to the oil production rule of *Mucor circinelloides*, a whole fermentation broth sample was collected and subjected to vacuum filtration with a Buchner funnel to obtain filtrate and filter cake. The filtrate was collected and stored at −20° C. for later use, and the filter cake were washed with distilled water for 3 times, and then freeze-dried to obtain freeze-dried cells for later use.

Acid treatment combined with repetitive freeze-thawing was carried out for breaking cell walls of freeze-dried recombinant bacteria Mc-glelo, from which then lipids were extracted with an organic solvent, referring to the method (Folch J, Lees M, Sloane-Stanley G, et al. A simple method for the isolation and purification of total lipids from animal tissues. Biol Chem, 1957, 226, 497-509) with appropriate modifications. The specific method was as follows: (1) after grinding the freeze-dried cells, weighing 20 mg dry weight of cells in a 5 mL glass bottle, and adding 2 mL of 4 M hydrochloric acid thereto; (2) subjecting the glass bottle to treatment in a 80° C. water bath for 1 h, and a −80° C. water bath for 15 min, and repeating the process once; (3) after the glass bottle returns to room temperature, adding 1 mL of methanol and 1 mL of chloroform, and adding 100 μL of internal standard C15:0 with a concentration of 2.02 μg/μL by a microsyringe; (4) subjecting the glass bottle to rotational extraction for 0.5 h with a mixer, followed by centrifugation at 3000 rpm for 3 min, and collecting a chloroform layer in a new 5 mL glass bottle; (5) adding 1 mL of chloroform to the original glass bottle again, repeating the process of (4) and combining the chloroform layers; (6) blowing with nitrogen for drying; (7) adding 1 mL solution of 10% hydrochloric acid in methanol, treating the original glass bottle in a 60° C. water bath for 3 h, during which the bottle was shaken for 30 sec every half an hour; (8) after the bottle was cooled to room temperature, adding 2 mL of n-hexane and 1 mL of saturated NaCl solution, vortexing to mix well, centrifuging at 4000 rpm for 3 min, sucking 1 mL of n-hexane layer, and transferring to a gas-phase bottle to obtain a fatty acid methyl ester solution.

Fatty acid methyl ester was analyzed by gas chromatography with commercially available fatty acid methyl ester standards (mixed standards of 37 fatty acid methyl esters) as standard samples. The gas chromatography was GC-6890N, Agilent, USA, and the measurement conditions were as follows: gas chromatography conditions: splitless sampling, DM-FFAP (30 m×0.32 mm, 0.22 μm) as chromatographic column, a hydrogen ion flame detector, nitrogen as the carrier gas, the temperature of a gasification chamber and the temperature of the detector both being 250° C., and a sample size of 1 μL. A temperature rising process was as follows: an initial temperature was 80° C., the temperature was first increased to 200° C. at a heating rate of 8° C./min, then increased to 205° C. at a heating rate of 1° C./min, and finally increased to 240° C. at a heating rate of 4° C./min, and kept at 240° C. for 5 min. Taking pentadecanoic acid (C15:0) as a reference, the size of the peak area of each fatty acid ingredient was recorded, and the total content of fatty acids was calculated. The results are as shown in Table 1, in which the intracellular lipid content of the over-expression strain Mc-glelo is increased, but is not significantly different from that of the control strain Mc1552.

TABLE 1

Lipid Contents of Fermentation-cultured Control Strain and glelo Over-expressing Strain

| fermentation time (h) | | 12 | 24 | 36 | 48 | 60 | 72 | 84 | 96 |
|---|---|---|---|---|---|---|---|---|---|
| strains | Mc-glelo | 3.98 | 5.45 | 10.5 | 11.35 | 13.85 | 15.75 | 15.38 | 14.97 |
| | Mc1552 | 5.90 | 9.31 | 11.86 | 12.39 | 12.40 | 12.86 | 13.21 | 13.04 |

The fatty acid composition of intracellular lipids of the over-expression strain Mc-glelo changed greatly, and dihomo-γ-linolenic acid appeared in the lipids of the over-expression strain Mc-glelo, and the content thereof reached 5.7% of the total fatty acids. The results are as shown in Table 2.

TABLE 2

Fatty Acid Composition of Lipids of Fermentation-cultured Control Strain and glelo Over-expressing Strain

| | | fatty acid composition (%) | | | | | |
|---|---|---|---|---|---|---|---|
| | | C(16:0) | C(18:0) | C(18:1) OA | C(18:2) LA | C(18:3) GLA | C(20:3) DGLA |
| strains | Mc-glelo | 27.281 | 9.439 | 21.481 | 14.486 | 21.59 | 5.726 |
| | Mc1552 | 18.41 | 4.22 | 31.18 | 16.72 | 29.45 | 0 |

(2) Determination of fatty acid composition and content of *Mucor circinelloides* recombinant strain Mc-glelo under optimized fermentation conditions Preparation of sample to be tested: the *Mucor circinelloides* recombinant strain Mc-glelo was cultured in a 2 L fermentation tank using modified Kendrick medium (adding safflower oil rich in linoleic acid to the medium). The fermentation conditions were as follows: 28° C., 700 rpm, an air inflow of 1 v/v min$^{-1}$, and pH being maintained at 6.0. According to the oil production rule of *Mucor circinelloides*, a whole fermentation broth sample was collected and subjected to vacuum filtration with a Buchner funnel to obtain filtrate and filter cake of cells, the filtrate was collected and stored at −20° C. for later use, and the filter cake were washed with distilled water for 3 times, and then freeze-dried to obtain freeze-dried cells for later use.

Acid treatment combined with repetitive freeze-thawing was carried out for breaking cell walls of freeze-dried recombinant bacteria Mc-glelo, from which then lipids were extracted with an organic solvent, referring to the method (Folch J, Lees M, Sloane-Stanley G, et al. A simple method for the isolation and purification of total lipids from animal tissues. Biol Chem, 1957, 226, 497-509) with appropriate modifications. The specific method was as follows: (1) after grinding the freeze-dried cells, weighing 20 mg dry weight of cells in a 5 mL glass bottle, and adding 2 mL of 4 M hydrochloric acid thereto; (2) subjecting the glass bottle to treatment in a 80° C. water bath for 1 h, and a −80° C. water bath for 15 min, and repeating the process once; (3) after the glass bottle returns to room temperature, adding 1 mL of methanol and 1 mL of chloroform, and adding 100 μL of internal standard C15:0 with a concentration of 2.02 μg/μL by a microsyringe; (4) subjecting the glass bottle to rotational extraction for 0.5 h with a mixer, followed by centrifugation at 3000 rpm for 3 min, and collecting a chloroform layer in a new 5 mL glass bottle; (5) adding 1 mL of chloroform to the original glass bottle again, repeating the process of (4) and combining the chloroform layers; (6) blowing with nitrogen for drying; (7) adding 1 mL solution of 10% hydrochloric acid in methanol, treating the original glass bottle in a 60° C. water bath for 3 h, during which the bottle was shaken for 30 sec every half an hour; (8) after the bottle was cooled to room temperature, adding 2 mL of n-hexane and 1 mL of saturated NaCl solution, vortexing to mix well, centrifuging at 4000 rpm for 3 min, sucking 1 mL of n-hexane layer, and transferring to a gas-phase bottle to obtain a fatty acid methyl ester solution.

Fatty acid methyl ester was analyzed by gas chromatography with commercially available fatty acid methyl ester standards (mixed standards of 37 fatty acid methyl esters) as standard samples. The gas chromatography was GC-6890N, Agilent, USA, and the measurement conditions were as follows: gas chromatography conditions: splitless sampling, DM-FFAP (30 m×0.32 mm, 0.22 μm) as chromatographic column, a hydrogen ion flame detector, nitrogen as the carrier gas, the temperature of a gasification chamber and the temperature of the detector both being 250° C., and a sample size of 1 μL. A temperature rising process was as follows: an initial temperature was 80° C., the temperature was first increased to 200° C. at a heating rate of 8° C./min, then increased to 205° C. at a heating rate of 1° C./min, and finally increased to 240° C. at a heating rate of 4° C./min, and kept at 240° C. for 5 min. Taking pentadecanoic acid (C15:0) as a reference, the size of the peak area of each fatty acid ingredient was recorded, and the total content of fatty acids was calculated. The results are as shown in Table 3, in which the intracellular lipid content of the over-expression strain Mc-glelo is increased.

TABLE 3

Lipid Contents of Fermentation-cultured Control Strain and glelo Over-expressing Strain

| fermentation time (h) | | 12 | 24 | 36 | 48 | 60 | 72 | 84 | 96 |
|---|---|---|---|---|---|---|---|---|---|
| strains | Mc-glelo | 4.0 | 6.2 | 11.8 | 14.9 | 15.2 | 15.5 | 15.6 | 15.9 |
| | Mc1552 | 5.8 | 9.4 | 11.5 | 12.2 | 12.7 | 12.6 | 13.3 | 13.2 |

The fatty acid composition of intracellular lipids of the over-expression strain Mc-glelo changed greatly, and DGLA appeared in the lipids of the over-expression strain Mc-glelo, and the content thereof reached 7.6% of the total fatty acids. The results are as shown in Table 4.

TABLE 4

Fatty Acid Composition of Lipids of Fermentation-cultured Control Strain and glelo Over-expressing Strain

| | | fatty acid composition (%) | | | | | |
|---|---|---|---|---|---|---|---|
| | | C(16:0) | C(18:0) | C(18:1) OA | C(18:2) LA | C(18:3) GLA | C(20:3) DGLA |
| strains | Mc-glelo | 24.6 | 2.7 | 22.6 | 18.8 | 23.7 | 7.6 |
| | Mc1552 | 18.5 | 4.3 | 31.3 | 16.7 | 29.6 | 0 |

INDUSTRIAL APPLICABILITY

The present disclosure provides a construction method of a *Mucor circinelloides* cell factory for producing dihomo-γ-linolenic acid and a fermentation technology thereof; the content of DGLA in the recombinant strain Mc-glelo can reach 5.7% of the total fatty acids, and the content of DGLA reaches 7.6% by adding precursor fatty acids and optimizing the fermentation conditions. Thus, the recombinant strain Mc-glelo can be used for producing dihomo-γ-linolenic acid.

The invention claimed is:

1. A recombinant cell producing dihomo-γ-linolenic acid, wherein the recombinant cell comprises a polynucleotide encoding γ-linolenic acid elongase, the polynucleotide encoding γ-linolenic acid elongase being operably linked to a promoter capable of driving expression of the polynucleotide in the recombinant cell;
wherein the polynucleotide encoding γ-linolenic acid elongase comprises:
a polynucleotide sequence shown in SEQ ID NO: 1;
wherein the recombinant cell is a *Mucor circinelloides* cell; and
wherein the recombinant cell is a recombinant strain deposited on Jun. 20, 2018 in China General Microbiological Culture Collection Center with an accession number of CGMCC No. 15887.

2. The recombinant cell according to claim 1, wherein the recombinant cell is not derived from *Mortierella alpina*.

3. A method for producing dihomo-γ-linolenic acid, wherein the method comprises fermenting the recombinant cell producing dihomo-γ-linolenic acid according to claim 1.

4. The method according to claim 3, wherein the fermentation is performed in a fermentation medium comprising γ-linolenic acid, γ-linolenic acid compounds or precursor compounds of γ-linolenic acid.

5. The method according to claim 4, wherein the fermentation medium comprises linoleic acid and/or linoleic acid compounds.

6. The method according to claim 4, wherein the fermentation medium comprises vegetable oil containing linoleic acid and/or linoleic acid compounds.

7. The method according to claim 6, wherein the vegetable oil is safflower seed oil or sunflower seed oil.

8. The method according to claim 6, wherein the vegetable oil is initially present in the fermentation medium, or is added to the fermentation medium by feeding during the fermentation.

9. The method according to claim 5, wherein the fermentation medium comprises vegetable oil containing linoleic acid and/or linoleic acid compounds.

* * * * *